(12) United States Patent
Nelson et al.

(10) Patent No.: US 10,017,467 B2
(45) Date of Patent: Jul. 10, 2018

(54) ALKYLBENZENE HYDROPEROXIDE PRODUCTION USING DISPERSED BUBBLES OF OXYGEN CONTAINING GAS

(71) Applicant: SABIC GLOBAL TECHNOLOGIES B.V., Bergen op Zoom (NL)

(72) Inventors: Mark Erik Nelson, Mt. Vernon, IN (US); Andrey Vladimirovich Zinenkov, St. Petersburg (RU); Arkady Samuilovich Dykman, St. Petersburg (RU)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/501,187

(22) PCT Filed: Aug. 7, 2015

(86) PCT No.: PCT/IB2015/056012
§ 371 (c)(1),
(2) Date: Feb. 2, 2017

(87) PCT Pub. No.: WO2016/020889
PCT Pub. Date: Feb. 11, 2016

(65) Prior Publication Data
US 2017/0210708 A1   Jul. 27, 2017

(30) Foreign Application Priority Data

Aug. 8, 2014 (RU) ................................ 2014132769

(51) Int. Cl.
| | | |
|---|---|---|
| C07C 407/00 | (2006.01) |
| C07C 37/08 | (2006.01) |
| C07C 45/53 | (2006.01) |
| B01J 10/00 | (2006.01) |
| B01J 19/00 | (2006.01) |
| B01J 19/24 | (2006.01) |

(52) U.S. Cl.
CPC ........... *C07C 407/00* (2013.01); *B01J 10/002* (2013.01); *B01J 19/0006* (2013.01); *B01J 19/248* (2013.01); *C07C 37/08* (2013.01); *C07C 45/53* (2013.01); *B01J 2219/00166* (2013.01); *B01J 2219/00177* (2013.01)

(58) Field of Classification Search
CPC ....... C07C 407/00; C07C 37/08; C07C 45/53; B01J 10/002
USPC ......................................... 568/558, 568, 798
See application file for complete search history.

(56) References Cited

U.S. PATENT DOCUMENTS 7,439,404 B2   10/2008   Kuma et al.

FOREIGN PATENT DOCUMENTS

| | | |
|---|---|---|
| EP | 1721895 A1 | 11/2006 |
| EP | 1932583 A1 | 6/2008 |
| WO | 2004108640 A2 | 12/2004 |

OTHER PUBLICATIONS

International Search Report for International Application No. PCT/IB2015/056012; International Filing Date: Aug. 7, 2015; dated Dec. 9, 2015; 5 Pages.
Written Opinion for International Application No. PCT/IB2015/056012; International Filing Date: Aug. 7, 2015; dated Dec. 9, 2015; 7 Pages.

*Primary Examiner* — Sikarl A Witherspoon
(74) *Attorney, Agent, or Firm* — Cantor Colburn LLP

(57) ABSTRACT

An apparatus for oxidation of a $C_8$-$C_{12}$ alkylbenzene reactant to a $C_8$-$C_{12}$ alkylbenzene hydroperoxide product, the reactor can comprise: a flow reactor comprising a reactant inlet, an oxidate product outlet, wherein the reactor is configured to provide a liquid flow from the reactant inlet to the product outlet, a gas inlet configured to introduce an oxygen-containing gas into the reactor, and an inlet sparger configured to flow gas bubbles comprising the oxygen-containing gas within the liquid flow, and wherein: the inlet sparger is configured to flow the gas bubbles having a diameter of 1.0 mm to 5.0 mm over a gas bubble residence time from 1 to 200 seconds, and/or the inlet sparger configured to flow the gas bubbles such that greater than or equal to 80% of the gas bubbles do not coalesce into larger bubbles over a gas bubble residence time of 1 to 200 seconds.

21 Claims, 1 Drawing Sheet

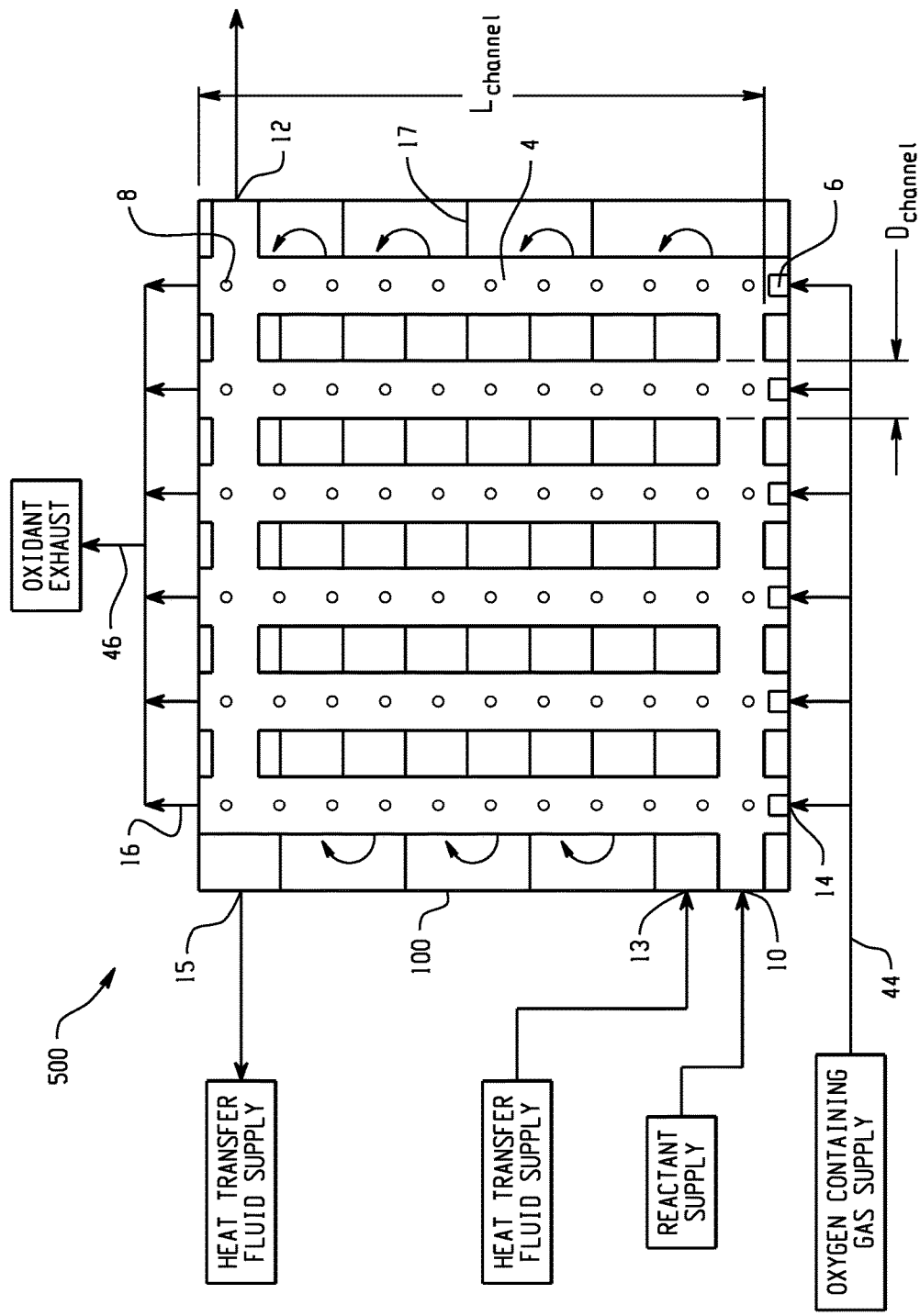

ALKYLBENZENE HYDROPEROXIDE PRODUCTION USING DISPERSED BUBBLES OF OXYGEN CONTAINING GAS

CROSS REFERENCE TO RELATED APPLICATIONS

This application is a 371 of International Application No. PCT/IB32015/056012, filed Aug. 7, 2015, which claims priority to Russian Application No. 2014132769, filed Aug. 8, 2014 which are incorporated herein by reference in their entirety.

BACKGROUND

A two-stage method of producing benzyl alcohol and ketone can involve continuously oxidizing an alkylbenzene with oxygen to form an intermediate, an alkylbenzene hydroperoxide. For example, oxidation of the alkylbenzene cumene, also referred to as isopropylbenzene, to produce the alkylbenzene hydroperoxide cumene hydroperoxide (CHP) is shown in reaction (I).

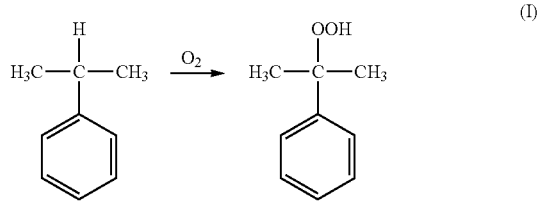
(I)

As shown in reaction (II), the intermediate CHP can then undergo acid decomposition with a protic acid to form phenol and acetone. The mixture of phenol and acetone that is formed in the process can then be separated and purified such as by rectification on a column.

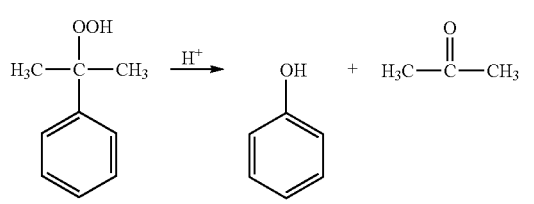
(II)

The economic efficiency of phenol and ketone synthesis by the alkylbenzene oxidation method can depend on attaining the highest possible yield in process of alkylbenzene oxidation and the two stage alkylbenzene hydroperoxide decomposition (also referred to as the cleavage stage). The yield of alkylbenzene hydroperoxide obtained during the oxidation process can be a function of the steady-state concentration maintained in the reaction vessel. Various competing side reactions can form undesirable byproducts and can reduce the product yield of the oxidation process. Insufficient mass transfer area between an alkylbenzene liquid phase and an oxidant gas phase can further reduce the product yield, increase the capitol cost of processing equipment, increase the size of processing equipment, increase the complexity of processing equipment, as well as decrease the process efficiency.

Accordingly, there remains a need in the art for an improved alkylbenzene oxidation process that can reduce the capital cost of the processing equipment, reduce the size of the processing equipment, increase the product yield, reduce the processing cost, reduce the formation of by-products, or can achieve a combination including at least one of the foregoing improvements.

BRIEF DESCRIPTION

In an embodiment, an apparatus for oxidation of a $C_8$-$C_{12}$ alkylbenzene reactant to a $C_8$-$C_{12}$ alkylbenzene hydroperoxide product can comprise: a flow reactor comprising a reactant inlet, an oxidate product outlet, wherein the reactor is configured to provide a liquid flow from the reactant inlet to the product outlet, a gas inlet configured to introduce an oxygen-containing gas into the reactor, and an inlet sparger configured to flow gas bubbles comprising the oxygen-containing gas within the liquid flow, a reaction channel, wherein, in use, the liquid flow from the reactant inlet to the oxidate product outlet is through a reaction channel, and wherein: the inlet sparger is configured to flow the gas bubbles having a diameter of 1.0 mm to 5.0 mm over a gas bubble residence time from 1 to 200 seconds, and/or the inlet sparger configured to flow the gas bubbles such that greater than or equal to 80% of the gas bubbles do not coalesce into larger bubbles over a gas bubble residence time of 1 to 200 seconds.

In another embodiment, an apparatus for oxidation of a $C_8$-$C_{12}$ alkylbenzene reactant to a $C_8$-$C_{12}$ alkylbenzene hydroperoxide product, can comprising: a flow reactor comprising a reactant inlet, an oxidate product outlet, wherein the reactor is configured to provide a liquid flow from the reactant inlet to the product outlet, a gas inlet configured to introduce an oxygen-containing gas into the reactor, an inlet sparger configured to flow gas bubbles comprising the oxygen-containing gas within the liquid flow, and a reaction channel, wherein, in use, the liquid flow from the reactant inlet to the oxidate product outlet is through a reaction channel, and wherein the inlet sparger has a single aperture configured to flow gas bubbles one at a time, serially, into the reaction channel.

In an embodiment, a process for the continuous production of a $C_8$-$C_{12}$ alkylbenzene hydroperoxide, can comprise: introducing a liquid flow comprising $C_8$-$C_{12}$ alkylbenzene through a reactant inlet to a reaction channel in a flow reactor; introducing gas bubbles to the reaction channel, wherein the gas bubbles have a diameter of 1.0 mm to 5.0 mm over a gas bubble residence time from 1 to 200 seconds, and/or wherein greater than or equal to 80% of the gas bubbles do not coalesce into larger bubbles over the gas bubble residence time of 1 to 200 seconds; and oxidizing the $C_8$-$C_{12}$ alkylbenzene to produce a liquid oxidate product comprising the $C_8$-$C_{12}$ alkylbenzene hydroperoxide.

In another embodiment, a process for the continuous production of a $C_8$-$C_{12}$ alkylbenzene hydroperoxide, can comprise: introducing a liquid flow comprising $C_8$-$C_{12}$ alkylbenzene through a reactant inlet to a reaction channel in a flow reactor; introducing gas bubbles, one at a time, serially, to the reaction channel through a single aperture in an inlet sparger; and oxidizing the $C_8$-$C_{12}$ alkylbenzene to produce a liquid oxidate product comprising the $C_8$-$C_{12}$ alkylbenzene hydroperoxide.

The above described and other features are exemplified by the following figures and detailed description.

BRIEF DESCRIPTION OF THE DRAWINGS

Refer now to the FIGURE, which is an exemplary embodiment.

FIG. 1 is an illustration of a co-flow alkylbenzene oxidation process.

DETAILED DESCRIPTION

The production of phenol and ketone can be a two stage process. The first stage can include the oxidation of alkylbenzene to alkylbenzene hydroperoxide. This oxidation stage can have a large effect on the overall product yield of the process. The oxidation stage can include introduction of an oxygen-containing gas to a liquid alkylbenzene phase in a reaction vessel to form the alkylbenzene hydroperoxide product phase. Various parameters can affect the product yield including the mass transfer surface area, or interfacial area, between the liquid alkylbenzene phase and the oxygen-containing gas phase, the oxygen content of the oxygen-containing gas, the alkylbenzene content of the liquid alkylbenzene phase, the residence time of the reactants (e.g., alkylbenzene, oxygen-containing gas), the temperature of the reacting mixture, the pressure of the reacting mixture, the presence of an oxidation catalyst, an oxidation catalyst concentration, an oxidation catalyst surface area, or a combination including at least one of the foregoing. Disclosed herein are an improved alkylbenzene oxidation apparatus and methods of using the same.

An apparatus for oxidation of an alkylbenzene reactant to form an alkylbenzene hydroperoxide product can include a flow reactor including a liquid alkylbenzene reactant inlet, an oxygen-containing gas reactant inlet, an alkylbenzene hydroperoxide product outlet, and an oxygen-containing gas outlet. The oxygen-containing gas inlet can be configured to introduce an oxygen-containing gas into the reactor. The oxygen-containing gas can be introduced to the alkylbenzene phase by bubbling it through the liquid alkylbenzene phase. The oxygen-containing gas reactant inlet can include a sparger which can be configured to feed a gas bubble of the oxygen-containing gas to the alkylbenzene liquid reactant phase.

The sparger can be a device including a flow inlet and a flow outlet. The flow outlet can include a single aperture for allowing a single stream of individual oxygen-containing gas bubbles to flow from the sparger serially (e.g., one at a time). The flow outlet can include a plurality of apertures to allow a plurality of dispersed bubbles of oxygen-containing gas to flow from the sparger (e.g., simultaneously). An aperture of the sparger can have a diameter of 0.01 millimeter (mm) to 10 mm, for example, 0.01 mm to 2 mm. An aperture of the sparger can have a length of 2 to 100 mm, for example, 2 mm to 50 mm, or, 5 mm to 25 mm. The sparger can have any cross-sectional shape, e.g., circular, elliptical, polygonal having straight or curved edges. The sparger can be arranged in a pattern, and a pattern can have any shape, e.g., spiral, serpentine, ring(s), gridded, radial, and the like. The pattern can be formed in a single plane or in multiple planes (e.g., terraced).

The sparger can be made of any material suitable for exposure to a temperature of 5° C. to 150° C., for example, 5° C. to 130° C., or, 5° C. to 110° C., to a pressure of 0 kiloPascal (gauge) (kPa(g)) to 1,400 kPa(g), for example, 0 kPa(g) to 1,000 kPa(g), or 0 kPa(g) to 600 kPa(g), and to a pH level of 4 to 10, for example, 4.5 to 10, or 6.5 to 7.5, and resistant to cumene, cumene hydroperoxide, water/sodium carbonate solution. The sparger can be constructed of metal, ceramic, plastic, or a combination comprising at least one of the foregoing. In an embodiment, the sparger is constructed of a metal conduit coupled to a porous ceramic gas distributing head including a plurality of flow channels. In another embodiment, the sparger is constructed of a metal conduit coupled to a porous metallic open-cell foam gas distributing head including a plurality of flow channels. The plurality of flow channels can be uniformly distributed over the surface of the sparger. The plurality of flow channels can be non-uniformly distributed over the surface of the sparger. In yet another embodiment, the sparger can include a single outlet aperture which can provide a single series of bubbles. The sparger can include a single outlet aperture and can be free of a gas distributing head.

The sparger can be configured to flow oxygen-containing gas bubbles having an average diameter of 1.0 millimeter (mm) to 5.0 mm, for example 2.0 mm to 4.0 mm, or 2.0 mm to 3.0 mm, as determined within a distance of less than or equal to 0.5 meters (m) from the sparger. The sparger can be configured to provide a flow of oxygen-containing gas bubbles to the reactor in such a way that the likelihood that the gas bubbles will coalesce as they flow in the liquid phase is decreased or eliminated. The sparger can be configured to flow the gas bubbles such that greater than or equal to 80% of the gas bubbles do not coalesce into larger bubbles over a gas bubble residence time of 1 to 200 seconds, for example 1 to 150 seconds, or, 1 to 100 seconds. The sparger can provide a gas bubble distribution which can include a bubble size distribution (e.g., distribution of bubble diameters, gas volumes, cross-sectional areas, and/or shapes), a spatial distribution (e.g., distribution within the cross-sectional area and/or volume of the liquid phase), a flow rate distribution (e.g., through a volume of the liquid phase, through sections of the sparger, and the like), or at least one of the foregoing.

The sparger can be configured to provide a bubble size distribution where the standard deviation of the gas bubble diameter of the bubbles flowing from the sparger can be less than or equal to 0.1 mm, for example, 0.05 mm, as determined within a distance of less than or equal to 0.25 meters (m) from the sparger surface. When the sparger is configured with a plurality of apertures, it can be configured to provide a spatial distribution of bubbles. For example, a distribution of bubbles where the standard deviation of the distance between the geometric center of any two adjacent bubbles (within a cross-section perpendicular to the reactor) is less than or equal to 10 mm, for example, 5 mm, or, 2.5 mm, as determined within a distance of less than or equal to 0.5 meters (m) from the sparger surface. The sparger can be configured to provide a flow rate distribution of gas, for example, where the standard deviation of the velocity of the gas bubbles less than or equal to 0.02 meters per second (m/s), for example, 0.01 m/s, or, 0.005 m/s, as determined within a distance of less than or equal to 0.5 meters (m) from the sparger surface.

The described gas bubble distributions, and size (e.g., diameter) of the gas bubbles can change as the bubbles flow through the liquid phase (e.g., as oxygen moves out of the gas phase and into the liquid phase). As a result the aforementioned characteristics of the bubbles and/or bubble distributions can vary as a function of the distance from the sparger. Therefore each of these characteristics can be determined within a distance of less than or equal to 0.25 meters (m) from the sparger surface.

Applicant is not required to provide a description of the theory of operation of the invention and the appended claims should not be limited by applicant's statements regarding such theory, but it is thought that the oxidation reactor efficiency can be affected by the gas bubble size in the following ways. The oxygen-containing gas bubble can be approximated by a sphere having a diameter, $d$, as the forces of surface tension can tend to minimize the ratio of surface area (see I) to volume (see II).

$$\text{Sphere Surface Area } = SA = 2\pi d^2 \quad \text{(I)}$$

$$\text{Sphere Volume} = V = \frac{2\pi d^3}{3} \quad \text{(II)}$$

In small scale laboratory testing it has been observed that as an oxygen-containing gas bubble moves through the liquid phase it can contact another bubble and the two bubbles can coalesce into a single larger bubble. From (I) and (II) it can be determined that as the diameter of the bubble (approximating a sphere) increases the volume of gas within the bubble can increase more rapidly than the surface area (e.g., as volume is proportional to the diameter cubed while surface area is proportional to the diameter squared). For example, the surface area to volume ratio (see III) can decease with increasing bubble diameter.

$$\text{Surface Area to Volume ratio} = \frac{SA}{V} = \frac{6}{d} \quad \text{(III)}$$

It is thought that the amount of oxygen transfer to the liquid phase is proportional to the surface area of the bubble, so as a bubble volume gets larger and the surface area to volume ratio decreases, the ratio of the amount of oxygen transferred to the liquid phase to bubble volume also decreases. Therefore, larger bubbles can have a lower ratio of oxygen mass transfer to the liquid phase to the bubble volume. Thus, an oxidation reactor having larger bubbles can have lower oxygen consumption efficiency (e.g., the ratio of the amount of oxygen consumed divided by the amount of oxygen fed to the reactor) in comparison to reactors with smaller bubbles. As a result, larger reactors can be needed to achieve the desired conversion (e.g., of oxygen) when the oxygen-containing gas bubbles are large.

In addition to the phenomenon described in the foregoing, larger bubbles can further reduce reactor efficiency as a) they can move faster due to their larger buoyant force, which can propel the larger bubbles into smaller bubbles and result in more coalescing, b) when a gas bubble flows upward through the liquid phase, the pressure can decrease (due to a decreasing pressure head) thus allowing the gas bubble to expand and become larger, reinforcing (a).

These phenomena can occur more frequently when a plurality of bubbles simultaneously flow from a sparger into a column of liquid (e.g., as bubbles can be diverted radially, within a cross sectional plane of the reactor, by various forces and coalesce). Conversely, when a sparger releases bubbles into a liquid column serially, such that each bubble is allowed to form and move a distance from the sparger prior to the formation and/or movement of the subsequent bubble, there is a reduced likelihood that the series of bubbles can interact with one another. Unlike a plurality of simultaneously formed bubbles, the serial bubbles can move radially (in a cross-sectional plane of the reactor) without encountering other bubbles, thereby reducing the likelihood that two or more bubbles can coalesce.

With this in mind, the sparger can be configured to provide a serial stream of oxygen-containing gas bubbles to a reactor. The reactor can include a single reaction channel. The reactor can include a single reaction channel in thermal communication with a heat transfer function such as a jacketed tube having a heat transfer fluid disposed around a portion of the tube. The reactor can include a plurality of separate channels disposed in thermal communication with a heat transfer media. In this case, a sparger can be configured to serially flow a single stream of oxygen-containing gas bubbles through each of the plurality of channels. The flow of oxygen-containing gas through the plurality of channels can be simultaneous (e.g., serial flow through each channel at the same time). The sparger can include a single oxygen-containing gas inlet and a plurality of gas outlets configured to provide the single stream of oxygen-containing gas to each channel. A sparger can have a single inlet and a single outlet and can be disposed in fluid communication with each channel, such that each channel of the plurality of channels has a corresponding sparger device. In an embodiment, the flow reactor can include a shell and tube heat exchanger where the oxidation is carried out in the tubes and a heat transfer cooling fluid can be disposed on the shell side of said heat exchanger.

FIG. 1 is an illustration of an alkylbenzene oxidation process 500 being carried out in a flow reactor 100 illustrated in cross-section. The flow reactor 100 can include a reactant inlet 10, a gas inlet 14, an inlet sparger 6, and an oxidate product outlet 12. An oxidation reaction can be carried out in the flow reactor 100. The flow reactor 100 can have a length, L.

The oxidation reaction can be carried out in the presence of an oxidation catalyst. The oxidation reaction can be carried out in a reaction channel 4. The reaction channel 4 can have a channel diameter, or equivalent diameter (e.g., when the cross sectional shape is not circular), of $D_{channel}$ and a channel length, $L_{channel}$. The length, $L_{channel}$, of the reaction channel 4 can be defined by the distance along the longest dimension of the channel where an oxygen-containing gas interfaces a liquid reactant. The reaction channel can have any cross sectional shape (e.g. circular, oval, any closed polygon with straight or curved edges). The flow reactor 100 can include a plurality of reaction channels 4. The plurality of reaction channels 4 can have a parallel arrangement. The plurality of reaction channels 4 can be uniformly spaced (e.g., where each tube is an equal distance from an adjacent tube). The flow reactor 100 can include an inlet sparger 6 configured to flow gas bubbles 8 of an oxygen-containing gas into the flow reactor 100.

The inlet sparger 6 can be configured to flow a single series of gas bubbles 8 along a reaction channel 4, such that the likelihood of coalescence between gas bubbles 8 is reduced. The inlet sparger 6 can be configured with a single inlet and a single outlet positioned to provide a single series of gas bubbles 8 to a reaction channel 4. The inlet sparger 6 can be configured with a single inlet and a plurality of outlets positioned so as to provide the flow of oxygen-containing gas as a single series of gas bubbles 8 to each of a plurality of reaction channels 4. The reaction channel 4 can be oriented such that gas bubbles 8 of the oxygen-containing gas can flow concurrent with the liquid reactant (e.g., in a co-flow arrangement). The reactant inlet 10 and oxidate product outlet 12 can be positioned such that the flow direction of the liquid reactant can be countercurrent with the direction of the oxygen-containing gas flow (e.g., in a counter-flow arrangement where the liquid reactant flow opposes the flow of the gas bubbles 8).

The flow reactor 100 can include a plurality of gas inlets 14. Each of a plurality of gas inlets 14 can be in fluid communication with a single reaction channel 4 (e.g., a one-to-one ratio of gas inlets 14 to reactor tubes 4). A gas inlet 14 can be co-axially aligned with a reaction channel 4, such that oxygen-containing gas can be directed along a center axis of the reaction channel 4. The oxygen content of the oxygen-containing gas can be reduced as it moves through the flow reactor 100 which can be the result of reaction with the liquid reactant. The oxygen content of the oxygen-containing gas supply 44 can be greater than or equal to 20 volume percent on a dry basis (vol. % dry), for example, 20 vol. % dry-50 vol. % dry, or, 20 vol. % dry-30 vol. % dry. The oxygen content of the gas exiting the flow reactor 100 at a gas outlet 16 can be the same as the oxygen content of the gas entering the reactor at the gas inlet 14 when no oxidation reaction is taking place. Once the oxidation reaction starts, the oxygen content of the oxygen-containing gas flowing through the gas outlet 16 can be less than 20 vol. % dry, for example, 2 vol. % dry to 18 vol. % dry, or 3 vol. % dry to 8 vol. % dry, or, 4 vol. % dry to 6 vol. % dry. The flow reactor 100 can include a plurality of gas outlets 16. Each of a plurality of gas outlets 16 can be in fluid communication with a single reaction channel 4 (e.g., a one-to-one ratio of gas outlets 16 to reaction channels 4). A gas outlet 16 can be co-axially aligned with a reaction channel 4. A plurality of gas outlet 16 can be combined into a single outlet 46. A plurality of gas outlet 16 from more than one flow reactor 100 can be combined into a single outlet 46.

The oxidation reaction is exothermic. Heat generated by the reaction can be removed from the flow reactor 100 by interaction with a heat transfer device. The heat transfer device can include any device that is capable of removing heat generated by the oxidation reaction. The heat transfer device can include a heat transfer fluid that can flow through the flow reactor 100. The heat transfer device can include a heat transfer fluid inlet 13, and a heat transfer fluid outlet 15. The heat transfer fluid inlet 13 and heat transfer fluid outlet 15 can be oriented such that a heat transfer fluid flows across the reaction channel 4 in a cross-flow pattern. The cross-flow pattern can include a serpentine pattern, such as directed by flow baffle 17. The heat transfer fluid inlet 13 and the heat transfer fluid outlet 15 can be disposed anywhere on the flow reactor 100. The heat transfer fluid inlet 13, heat transfer fluid outlet 15, and flow baffle 17 can be located and oriented to provide any desired flow configuration, such as co-flow, counter-flow, cross-flow, or a combination comprising at least one of the foregoing.

An alkylbenzene oxidation process 500 can include more than one flow reactor 100. Two or more flow reactors 100 of an alkylbenzene oxidation process 500 can be arranged in any flow arrangement. The liquid reactant stream of two or more flow reactors 100 can be in fluid communication such that the liquid reactant flow includes a serial flow arrangement, a parallel flow arrangement, or a combination of a serial flow arrangement and a parallel flow arrangement. For example, the liquid reactant flow of two or more flow reactors 100 can be arranged in a serial flow arrangement where the oxidate product outlet 12 of a first flow reactor 100 is fed to the reactant inlet 10 of a second flow reactor 100, which can continue to an $n^{th}$ flow reactor 100. A serial flow arrangement of the liquid reactant flow can allow the concentration of the oxidate product to build up as it passes through each reactor. Higher oxidate product concentration can be desirable as it can increase reactor productivity (e.g., alkylbenzene hydroperoxide cleavage).

The gas inlet 14 of two or more flow reactors 100 can be arranged in any flow arrangement. For example, a single oxygen-containing gas supply 44 can feed the two or more flow reactors 100 in a parallel flow arrangement, such that the flow from the oxygen-containing gas supply 44 can be split between the two or more flow reactors 100. A parallel flow arrangement of the oxygen-containing gas can allow for the gas inlet 14 of each flow reactor 100 to receive oxygen containing gas having an oxygen concentration of the oxygen-containing gas supply 44, which can improve reactor conversion, reduce the number of reaction channels 4 to achieve a desired conversion, reduce the size of the flow reactor 100, or a combination comprising at least one of the foregoing. An enricher can be provided to increase the oxygen concentration of the oxygen-containing gas. The enricher can be in fluid communication with the oxygen-containing gas supply 44, with the gas inlet 14 to a flow reactor 100, with the inlet sparger 6, or a combination comprising at least one of the foregoing.

The length of the flow reactor 100, height of the flow reactor 100, width of the flow reactor 100, number of reaction channels 4, diameter of the reaction channel 4, length of the reaction channel 4, flow arrangement, the liquid phase flow rate, the oxygen-containing gas flow rate, the configuration of the inlet sparger 6, the position of the inlet sparger 6 within the flow reactor 100, the size of the inlet sparger 6, the oxygen-containing gas pressure, or a combination comprising at least one of the foregoing can be configured to provide a residence time of a gas bubble 8 within the reactor of 1 to 200 seconds, for example, 1 to 150 seconds, or, 1 to 100 seconds. The reactor can be configured such that greater than or equal to 80% of the gas bubbles do not coalesce into larger bubbles over the gas bubble residence time of 1 to 200 seconds. The reactor can be configured such that greater than or equal to 80% of the gas bubbles do not coalesce into larger bubbles over the gas bubble residence time of greater than or equal to 5, or greater than or equal to 10 seconds, or even greater than or equal to 15 seconds.

The reaction channel 4 of the flow reactor 100 can include a length to inside diameter ratio (L/ID) of 5 to 200, for example 5 to 100, or 5 to 20. The reaction channel 4 of the flow reactor 100 can have an inside diameter of greater than or equal to 6 millimeter (mm), for example, 6 mm to 100 mm, or, 6 mm to 50 mm, or, 6 mm to 25 mm. The ratio of the average diameter of a gas bubble 8 to the diameter of the reaction channel 4 ($D_{bubble}/ID_{channel}$) can be less than or equal to 0.9, for example, 0.01 to 0.8, or 0.01 to 0.5.

By controlling the size, residence time, or both the size and residence time of the oxygen-containing gas bubbles 8 as they flow through the flow reactor 100 the desired conversion of alkylbenzene can be achieved with a reaction channel length of less than or equal to 30 meters (m), for example, 0.3 m to 30 m, or, 1 m to 10 m, or, 1 m to 5 m, or 1 m to 2 m. For example, when the oxygen content of the oxygen containing gas entering the flow reactor 100 at the gas inlet 14 is 20.9 vol. % dry, the desired conversion of alkylbenzene can correspond to an oxygen content of the oxygen-containing gas flowing through the gas outlet 16 of 3 vol. % wet to 8 vol. % wet, or, 3.5 vol. % wet to 4 vol. % wet as measured using an oxygen sensor located at the gas outlet 16. The wet basis can correspond to a temperature of 75° C. to 115° C., or 85° C. to 110° C. Thus, controlling the gas bubble size can allow a smaller reactor to achieve the same reaction conversion as a larger reactor where the gas bubbles are allowed to coalesce. As a result, the energy demand (e.g., blower power, supply pressure, and the like) of the oxygen containing gas supply system can be reduced accordingly.

The flow reactor 100 can be configured to provide a liquid flow from the reactant inlet 10 to the oxidate product outlet 12. The flow reactor 100 can be configured to have any flow orientation between the reactant streams. The flow reactor 100 can be configured to have any flow orientation relative to earth's gravitational field (e.g., horizontal flow perpendicular to Earth's gravity, vertical flow parallel with Earth's gravity, and flow at an angle relative to Earth's gravity). The flow orientation of the flow reactor 100 can be co-flow, where the reactant streams flow in the same direction through the reactor (excluding an entrance section, where the flow orientation of the reactants can be any orientation, such as intersecting each other). The flow orientation of the flow reactor 100 can be counter-flow, where the reactant streams flow in opposing directions through the flow reactor 100 (excluding an entrance section, where the flow orientation of the reactants can be any orientation, such as not intersecting each other). The flow orientation of the flow reactor 100 can be cross-flow, where one reactant stream flows at an angle (e.g., perpendicular) relative to the flow direction of the other reactant stream (excluding an entrance section, where the flow orientation of the reactants can be any orientation, such as not intersecting each other). The flow orientation between the two reactant streams can vary along the length of the flow reactor 100.

In an embodiment, the flow reactor 100 can be configured such that the oxygen-containing gas bubbles can flow downward (e.g., opposing gravity) in a co-flow arrangement with the liquid reactant phase. In this case, the gas bubbles can be compressed as they approach the bottom of the reactor by the increasing pressure of the liquid head and the likelihood that gas bubbles would coalesce would thus be reduced.

The alkylbenzene can include a $C_8$-$C_{12}$ alkylbenzene (e.g., cumene). The alkylbenzene hydroperoxide can include a $C_8$-$C_{12}$ alkylbenzene hydroperoxide (e.g., cumene hydroperoxide (CHP)). The oxygen-containing gas can include air, such as ambient air. The oxygen-containing gas source can include dried air having a water vapor concentration of less than or equal to 5 mass percent (mass %), for example, 0-1 mass %, or, 0-0.25 mass %, or, 0-0.001 mass %. The oxygen-containing gas can include oxygen enriched air having an $O_2$ concentration of greater than or equal to 20 volume percent on a dry basis (vol. % dry), for example, 20-50 vol. % dry, or, 20-30 vol. % dry. The decomposition product of the $C_8$-$C_{12}$ alkylbenzene hydroperoxide formed in oxidation can include phenol. The ketone formed in the decomposition of the $C_8$-$C_{12}$ alkylbenzene hydroperoxide can include a $C_3$-$C_6$ ketone (e.g., acetone).

The oxidation reaction may be carried out in the presence of catalyst or no catalyst. A catalyst for use in the oxidation can be an alkaline material (i.e., can be a base having a pH of greater than 7.0). Examples of alkaline material include carbonate and hydroxide compounds of alkali metal such as lithium, sodium and potassium, alkaline earth metal such as calcium and magnesium, or a combination of at least one of the foregoing. The alkaline materials can be provided in various forms, including in an aqueous solution. The amount of catalyst (metal basis) is usually not more than 10 gram (g) equivalent, for example, 0.1 g to 6 g equivalent per 1 ton (907 kilogram (kg)) of alkylbenzene.

The liquid reactant phase can include fresh alkylbenzene, recycled unreacted alkylbenzene, catalyst, pH control agents, unreacted oxygen-containing gas, or a combination comprising at least one of the foregoing. A greater mass flow rate of the liquid reactant can be fed to the reactor in comparison to the mass flow rate of oxygen in the oxygen-containing gas feed. The total steady state mass flow rate of oxygen fed into a flow reactor can be less than or equal to 50% of the total mass flow rate of the liquid reactant, for example, 5% to 50%, or, 10% to 20%, or, 10% to 15%.

The pH of the reaction mixture in the flow reactor can be controlled to 4 to 10, for example, 4.5 to 10, or 6.5 to 7.5. One strategy for controlling the pH can be the addition of an acid suppressing agent. An acid suppressing agent can include an alkaline reagent, e.g., ammonia, carbonate, or the like.

In an embodiment the alkylbenzene liquid reactant can include cumene, the oxygen-containing gas can include air, and the oxidation reaction product can include cumene hydroperoxide (CHP). In this case, a higher reactor temperature (e.g., 85° C. to 130° C.) can help to start the oxidation reaction. However, a lower temperature (e.g. 45° C. to 115° C.) can provide desirable reaction selectivity, such as converting a larger amount of cumene to CHP in comparison to the amount of cumene that is converted to other byproducts (e.g., dimethylbenzyl alcohol (DMBA), acetophenone (AP)). In addition to temperature, the interfacial area between the oxygen-containing gas phase and the liquid alkylbenzene phase can influence product yield. Therefore, reducing the reaction temperature while increasing the reaction interfacial area (e.g., gas surface area) can increase product yield and reduce by-product yield. It follows that by optimizing the oxygen-containing bubble size the oxidation process efficiency can be increased, the operational cost can be reduced, the capital cost can be reduced, the reactor size can be reduced, the plant size can be reduced, or a combination of at least one of the foregoing.

Embodiment 1: An apparatus for oxidation of a $C_8$-$C_{12}$ alkylbenzene reactant to a $C_8$-$C_{12}$ alkylbenzene hydroperoxide product, the reactor comprising: a flow reactor comprising a reactant inlet, an oxidate product outlet, wherein the reactor is configured to provide a liquid flow from the reactant inlet to the product outlet, a gas inlet configured to introduce an oxygen-containing gas into the reactor, and an inlet sparger configured to flow gas bubbles comprising the oxygen-containing gas within the liquid flow, a reaction channel, wherein, in use, the liquid flow from the reactant inlet to the oxidate product outlet is through a reaction channel, and wherein: the inlet sparger is configured to flow the gas bubbles having a diameter of 1.0 mm to 5.0 mm over a gas bubble residence time from 1 to 200 seconds, and/or the inlet sparger configured to flow the gas bubbles such that greater than or equal to 80% of the gas bubbles do not coalesce into larger bubbles over a gas bubble residence time of 1 to 200 seconds.

Embodiment 2: An apparatus for oxidation of a $C_8$-$C_{12}$ alkylbenzene reactant to a $C_8$-$C_{12}$ alkylbenzene hydroperoxide product, the reactor comprising: a flow reactor comprising a reactant inlet, an oxidate product outlet, wherein the reactor is configured to provide a liquid flow from the reactant inlet to the product outlet, a gas inlet configured to introduce an oxygen-containing gas into the reactor, an inlet sparger configured to flow gas bubbles comprising the oxygen-containing gas within the liquid flow, and a reaction channel, wherein, in use, the liquid flow from the reactant inlet to the oxidate product outlet is through a reaction channel, and wherein the inlet sparger has a single aperture configured to flow gas bubbles one at a time, serially, into the reaction channel.

Embodiment 3: The apparatus of any of Embodiments 1-2, wherein the inlet sparger is configured to flow the gas bubbles having a diameter of 1 to 5.0 mm over a gas bubble residence time of 1 to 150 seconds.

Embodiment 4: The apparatus of any one of Embodiments 1-3, wherein the inlet sparger configured to distribute gas bubbles such that greater than or equal to 80% of the gas bubbles do not coalesce into larger bubbles over the gas bubble residence time.

Embodiment 5: The apparatus of any one of Embodiments 1-4, wherein the inlet sparger configured to distribute gas bubbles such that 100% of the gas bubbles do not coalesce into larger bubbles over the gas bubble residence time.

Embodiment 6: The apparatus of any of Embodiments 1-5, further comprising an enricher configured to increase the oxygen levels in the oxygen-containing gas to greater than or equal to 30 volume % on a dry basis.

Embodiment 7: The apparatus of any of Embodiments 1-6, further comprising a pH control medium supply in fluid communication with the reactant inlet.

Embodiment 8: The apparatus of Embodiment 7, wherein the pH control medium supply comprises at least one of sodium carbonate, ammonia, and ammonia carbonate.

Embodiment 9: The apparatus of any of Embodiments 1-8, wherein the gas inlet is located to provide a flow of the gas bubbles which is concurrent with the liquid flow.

Embodiment 10: The apparatus of any of Embodiments 1-8, wherein the gas inlet is located to provide a flow of the gas bubbles which is countercurrent to the liquid flow.

Embodiment 11: The apparatus of any of Embodiments 1-8, wherein the gas inlet is located to provide a flow of the gas bubbles to the flow reactor, wherein the gas bubbles are introduced into the flow reactor in a direction across the a liquid flow direction and wherein the gas bubbles flow through the reactor in a direction with the liquid flow.

Embodiment 12: The apparatus of any of Embodiments 1-11, wherein the apparatus is configured such that the liquid flow from the reactant inlet to the oxidate product outlet is horizontal.

Embodiment 13: The apparatus of any of Embodiments 1-11, wherein the apparatus is configured such that the liquid flow from the reactant inlet to the oxidate product outlet is vertical.

Embodiment 14: The apparatus of any of Embodiments 1-11, wherein the apparatus is configured such that the liquid flow from the reactant inlet to the oxidate product outlet is at an angle between 1 and 89 degrees, or between 5 and 85 degrees.

Embodiment 15: The apparatus of any of Embodiments 1-14, wherein the liquid flow from the reactant inlet to the product outlet is through a reaction channel having a diameter of greater than or equal to 6 mm.

Embodiment 16: The apparatus of Embodiment 15, wherein the reaction channel diameter is less than or equal to 100 mm.

Embodiment 17: The apparatus of Embodiment 16, wherein the reaction channel diameter is 6 mm to 50 mm.

Embodiment 18: The apparatus of any of Embodiments 15-17, wherein the reaction channel has a length of 0.3 m to 30 m.

Embodiment 19: The apparatus of Embodiment 18, wherein the reaction channel length is 1 m to 5 m.

Embodiment 20: The apparatus of any of Embodiments 15-19, wherein the reaction channel is a tube from a heat exchanger bundle.

Embodiment 21: The apparatus of Embodiment 20, further comprising a fluid on a shell side of the reaction channel.

Embodiment 22: The apparatus of any of Embodiments 1-21, wherein the inlet sparger comprises an array of sparger channels, wherein each sparger channel has a diameter of 0.01 to 0.9 mm.

Embodiment 23: The apparatus of any of Embodiments 1-22, wherein the inlet sparger comprises an array of sparger channels, wherein each sparger channel has a length of 2 mm to 100 mm.

Embodiment 24: The apparatus of Embodiment 23, wherein each sparger channel length is 5 mm to 25 mm.

Embodiment 25: The apparatus of any of Embodiments 1-24, wherein the flow reactor further comprises a gas outlet comprising an oxygen sensor and/or a temperature sensor.

Embodiment 26: The apparatus of Embodiment 25, wherein the flow reactor further comprises a control system, wherein input signals to the control system comprise the oxygen sensor and the temperature sensor, and wherein the control system is configured to control an air compressor.

Embodiment 27: A system for the continuous production of cumene hydroperoxide comprising a reactor of any of Embodiments 1-26.

Embodiment 28: A process for the continuous production of a $C_8$-$C_{12}$ alkylbenzene hydroperoxide, comprising: introducing a liquid flow comprising $C_8$-$C_{12}$ alkylbenzene through a reactant inlet to a reaction channel in a flow reactor; introducing gas bubbles to the reaction channel, wherein the gas bubbles have a diameter of 1.0 mm to 5.0 mm over a gas bubble residence time from 1 to 200 seconds, and/or wherein greater than or equal to 80% of the gas bubbles do not coalesce into larger bubbles over the gas bubble residence time of 1 to 200 seconds; and oxidizing the $C_8$-$C_{12}$ alkylbenzene to produce a liquid oxidate product comprising the $C_8$-$C_{12}$ alkylbenzene hydroperoxide.

Embodiment 29: A process for the continuous production of a $C_8$-$C_{12}$ alkylbenzene hydroperoxide, comprising: introducing a liquid flow comprising $C_8$-$C_{12}$ alkylbenzene through a reactant inlet to a reaction channel in a flow reactor; introducing gas bubbles, one at a time, serially, to the reaction channel through a single aperture in an inlet sparger; and oxidizing the $C_8$-$C_{12}$ alkylbenzene to produce a liquid oxidate product comprising the $C_8$-$C_{12}$ alkylbenzene hydroperoxide.

Embodiment 30: The process of any of Embodiments 28-29, wherein the $C_8$-$C_{12}$ alkylbenzene is cumene and the $C_8$-$C_{12}$ alkylbenzene hydroperoxide is cumene hydroperoxide.

Embodiment 31: The process of any of Embodiments 28-30, further comprising controlling a pH of the reaction mixture from 4 to 10 by adding at least one of sodium carbonate or ammonia, or ammonia carbonate.

Embodiment 32: The process of any of Embodiments 28-31, wherein the oxidizing is at a reactor pressure of 0 kPa(g) to 1,400 kPa(g).

Embodiment 33: The process of any of Embodiments 28-32, wherein the oxidizing is at a temperature of 70° C. to 130° C.

Embodiment 34: The process of any of Embodiments 28-33, wherein the oxidizing is at a temperature of 90° C. to 110° C.

Embodiment 35: The process of any of Embodiments 28-34, wherein no water is added during the oxidation and wherein the oxidizing is at a temperature of 110° C. to 125° C.

Embodiment 36: The process of any of Embodiments 28-35, wherein the $C_{8-12}$ alkylbenzene is sec-butyl benzene and the $C_{8-12}$ alkylbenzene hydroperoxide is sec-butyl benzene hydroperoxide.

Embodiment 37: The process of any of Embodiments 28-36, comprising maintaining a gas outlet oxygen concentration of greater than or equal to 2 vol. % wet.

Embodiment 38: The process of Embodiment 37, wherein the gas outlet oxygen concentration is greater than or equal to 3 vol. % wet.

Embodiment 39: The process of Embodiment 37, wherein the gas outlet oxygen concentration is greater than or equal to 4 vol. % wet.

Embodiment 40: The process of any of Embodiments 28-39, comprising maintaining a temperature of the flow reactor of 175° C. to 225° C., and wherein the temperature comprises a gas outlet temperature of the flow reactor, an oxidate product outlet temperature of the flow reactor, or a combination comprising at least one of the foregoing.

Embodiment 41: The process of any of Embodiments 28-40, wherein passing comprises flowing at a fixed rate.

Embodiment 42: The process of any of Embodiments 28-41, adjusting a temperature of the flow reactor in response to a gas outlet oxygen concentration, wherein the temperature comprises a gas outlet temperature of the flow reactor, an oxidate product outlet temperature of the flow reactor, or a combination comprising at least one of the foregoing.

Embodiment 43: The process of Embodiment 42, wherein adjusting comprises decreasing the temperature if the gas outlet oxygen concentration is less than or equal to 3.5 vol. % wet, increasing the temperature if the gas outlet oxygen concentration is greater than or equal to 3.5 vol. % wet, or a combination comprising at least one of the foregoing.

Embodiment 44: A process for producing phenol and acetone, comprising oxidizing the $C_{8-12}$ alkylbenzene of any of Embodiments 28-43 in the presence of an oxygen-containing gas to produce a $C_{8-12}$ alkylbenzene hydroperoxide; and cleaving the $C_{8-12}$ alkylbenzene hydroperoxide in the presence of an acid catalyst to produce phenol and an acetaldehyde, a $C_{2-6}$ ketone, or a combination comprising at least one of the foregoing.

Embodiment 45: The process of Embodiment 44, wherein the cleavage is ammonia free.

Embodiment 46: The process of any of Embodiments 44-45, wherein the process is in the absence of ammonia.

Embodiment 47: The process of any of Embodiments 44-46, comprising adding 0 wt % ammonia.

Embodiment 48: The use of the phenol of any of Embodiments 44-47 to produce bisphenol A.

Embodiment 49: The use of the bisphenol A of Embodiment 48 to produce polycarbonate.

Embodiment 50: A method for the manufacture of bisphenol A, comprising reacting the phenol and/or acetone of any of Embodiments 44-47 in the presence of a catalyst to form bisphenol A.

Embodiment 51: A process for the production of polycarbonate, comprising contacting the bisphenol A of Embodiment 50 with a carbonyl source in the presence of a catalyst and under polycarbonate-forming conditions, to produce the polycarbonate.

Embodiment 52: A polycarbonate produced by the process of Embodiment 51.

Embodiment 53: The apparatus of any of Embodiments 1-27, wherein the gas inlet is located to provide a flow of the gas bubbles to the flow reactor, wherein the gas bubbles are introduced into the flow reactor in a direction perpendicular to the liquid flow and wherein the gas bubbles flow through the reactor in a direction which is substantially parallel to the liquid flow.

Embodiment 54: The apparatus of any of Embodiments 1-27 and 53, wherein greater than or equal to 80% of the gas bubbles do not coalesce into larger bubbles over the gas bubble residence time of greater than or equal to 5 seconds.

Embodiment 55: The apparatus of any of Embodiment 54, wherein greater than or equal to 80% of the gas bubbles do not coalesce into larger bubbles over the gas bubble residence time of greater than or equal to 10 seconds.

Embodiment 56: The apparatus of any of Embodiment 55, wherein greater than or equal to 80% of the gas bubbles do not coalesce into larger bubbles over the gas bubble residence time of greater than or equal to 15 seconds.

Embodiment 57: The apparatus of any of Embodiment 56, wherein greater than or equal to 90% of the gas bubbles do not coalesce.

Embodiment 58: The apparatus of any of Embodiments 1-27 and 53-57, wherein the oxygen-containing gas is air.

Embodiment 59: The apparatus of any of Embodiments 1-27 and 53-58, wherein only one inlet sparger is located in the reaction channel.

Embodiment 60: The process of any of Embodiments 28-43 wherein the gas bubbles have an initial size and a final size after the residence time, and wherein the initial size is less than or equal to the final size.

Embodiment 61: The process of any of Embodiments 28-43 and 60, further comprising distributing the gas bubbles in the reaction channel such that the bubbles do not coalesce in the reaction time.

Embodiment 62: The process of any of Embodiments 28-43, 60, and 61, wherein the liquid oxidate product further comprises dimethylbenzyl alcohol and acetophenone.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. % or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A reactor for oxidation of a $C_8$-$C_{12}$ alkylbenzene reactant to a $C_8$-$C_{12}$ alkylbenzene hydroperoxide product, the apparatus comprising:
a flow reactor comprising
a reactant inlet,
an oxidate product outlet, wherein the flow reactor is configured to provide a liquid flow from the reactant inlet to the oxidate product outlet,
a gas inlet configured to introduce an oxygen-containing gas into the flow reactor,
an inlet sparger configured to flow gas bubbles comprising the oxygen-containing gas within the liquid flow, and
a reaction channel, wherein, in use, the liquid flow from the reactant inlet to the oxidate product outlet is through a reaction channel, and
wherein the inlet sparger has a single aperture configured to flow gas bubbles one at a time, serially, into the reaction channel.

2. The reactor of claim 1 wherein:
the inlet sparger is configured to flow the gas bubbles having a diameter of 1.0 mm to 5.0 mm over a gas bubble residence time from 1 to 200 seconds, and/or
the inlet sparger configured to flow the gas bubbles such that greater than or equal to 80% of the gas bubbles do not coalesce into larger bubbles over a gas bubble residence time of 1 to 200 seconds.

3. The reactor of claim 2, wherein the inlet sparger is configured to flow the gas bubbles having a diameter of 1 to 5.0 mm over a gas bubble residence time of 1 to 150 seconds.

4. The reactor of claim 2, wherein the inlet sparger configured to distribute gas bubbles such that greater than or equal to 90% of the gas bubbles do not coalesce into larger bubbles over the gas bubble residence time.

5. The reactor of claim 2, further comprising an enricher configured to increase the oxygen levels in the oxygen-containing gas to greater than or equal to 30 volume % on a dry basis.

6. The reactor of claim 2, further comprising a pH control medium supply in fluid communication with the reactant inlet, and wherein the pH control medium supply comprises at least one of sodium carbonate, ammonia, and ammonium carbonate.

7. The reactor of claim 2, wherein the gas inlet is located to provide a flow of the gas bubbles to the flow reactor, wherein the gas bubbles are introduced into the flow reactor in a direction across a liquid flow direction and wherein the gas bubbles flow through the flow reactor in a direction coaxial with the liquid flow.

8. The reactor of claim 2, wherein the reaction channel has a diameter of greater than or equal to 6 mm.

9. The reactor of claim 2, wherein the inlet sparger comprises an array of sparger channels, wherein each sparger channel has a diameter of 0.01 to 0.9 mm.

10. The reactor of claim 2, wherein the flow reactor further comprises a gas outlet comprising an oxygen sensor and/or a temperature sensor, and wherein the flow reactor further comprises a control system, wherein input signals to the control system comprise signals from the oxygen sensor and the temperature sensor, and wherein the control system is configured to control an air compressor.

11. A process for the continuous production of a $C_8$-$C_{12}$ alkylbenzene hydroperoxide, comprising:
introducing a liquid flow comprising $C_8$-$C_{12}$ alkylbenzene through a reactant inlet to a reaction channel in the reactor of claim 2;
introducing gas bubbles to the reaction channel, wherein the gas bubbles have a diameter of 1.0 mm to 5.0 mm over a gas bubble residence time from 1 to 200 seconds, and/or wherein greater than or equal to 80% of the gas bubbles do not coalesce into larger bubbles over the gas bubble residence time of 1 to 200 seconds; and
oxidizing the $C_8$-$C_{12}$ alkylbenzene to produce a liquid oxidate product comprising the $C_8$-$C_{12}$ alkylbenzene hydroperoxide.

12. A process for the continuous production of a $C_8$-$C_{12}$ alkylbenzene hydroperoxide, comprising:
introducing a liquid flow comprising $C_8$-$C_{12}$ alkylbenzene through a reactant inlet to a reaction channel in the reactor of claim 1;
introducing gas bubbles, one at a time, serially, to the reaction channel through a single aperture in an inlet sparger; and
oxidizing the $C_8$-$C_{12}$ alkylbenzene to produce a liquid oxidate product comprising the $C_8$-$C_{12}$ alkylbenzene hydroperoxide.

13. The process of claim 11, wherein the $C_8$-$C_{12}$ alkylbenzene is cumene and the $C_8$-$C_{12}$ alkylbenzene hydroperoxide is cumene hydroperoxide, and/or wherein the liquid oxidate product further comprises dimethylbenzyl alcohol and acetophenone.

14. The process of claim 11, further comprising controlling a pH value of the reaction mixture from 4 to 10 by adding at least one of sodium carbonate or ammonia, or ammonium carbonate.

15. The process of claim 11,
wherein the oxidizing is at a reactor pressure of 0 kPa(g) to 1,400 kPa(g), and/or
wherein the oxidizing is at a temperature of 70° C. to 130° C.

16. The process of claim 11, wherein the $C_{8-12}$ alkylbenzene is sec-butyl benzene and the $C_{8-12}$ alkylbenzene hydroperoxide is sec-butyl benzene hydroperoxide.

17. The process of claim 11, comprising maintaining a gas outlet oxygen concentration of greater than or equal to 2 vol. % wet.

18. The process of claim 11, comprising maintaining a temperature of the flow reactor of 175° C. to 225° C., and wherein the temperature comprises a gas outlet temperature of the flow reactor, an oxidate product outlet temperature of the flow reactor, or a combination comprising at least one of the foregoing.

19. The process of claim 11, adjusting a temperature of the flow reactor in response to a gas outlet oxygen concentration, wherein the temperature comprises a gas outlet temperature of the flow reactor, an oxidate product outlet temperature of the flow reactor, or a combination comprising at least one of the foregoing.

20. A process for producing phenol and acetone, comprising
oxidizing the $C_{8-12}$ alkylbenzene of claim 11 in the presence of an oxygen-containing gas to produce a $C_{8-12}$ alkylbenzene hydroperoxide; and
cleaving the $C_{8-12}$ alkylbenzene hydroperoxide in the presence of an acid catalyst to produce phenol and a acetaldehyde, a $C_{2-6}$ ketone, or a combination comprising at least one of the foregoing.

21. The process of claim 19, wherein adjusting comprises decreasing the temperature if the gas outlet oxygen concentration is less than or equal to 3.5vol. % wet; increasing the temperature if the gas outlet oxygen concentration is greater than or equal to 3.5 vol. % wet, or a combination comprising at least one of the forgoing.

\* \* \* \* \*